United States Patent [19]

Frazier et al.

[11] Patent Number: 4,975,529

[45] Date of Patent: Dec. 4, 1990

[54] METHOD OF FOLDING SOMATOTROPINS

[75] Inventors: Ronald B. Frazier, Lake St. Louis, Mo.; Yasuo Konishi, St. Laurent, Canada

[73] Assignee: Monsanto Company, St. Louis, Mo.

[21] Appl. No.: 395,830

[22] Filed: Aug. 18, 1989

[51] Int. Cl.$^5$ .................... C07K 15/06; C07K 13/00; C07K 3/28; C12N 15/18

[52] U.S. Cl. .................... 530/399; 530/350; 530/412; 435/69.4

[58] Field of Search .................... 530/350, 399, 412; 435/68, 69.4

[56] References Cited

U.S. PATENT DOCUMENTS

| | | | |
|---|---|---|---|
| 4,599,197 | 7/1986 | Wetzel | 530/405 |
| 4,620,948 | 11/1986 | Builder et al. | 530/419 |
| 4,652,630 | 3/1987 | Bentle et al. | 530/344 |
| 4,656,255 | 4/1987 | Seely | 530/412 |
| 4,677,196 | 6/1987 | Rausch et al. | 530/412 |
| 4,705,848 | 11/1987 | Yang et al. | 530/399 |
| 4,731,440 | 3/1988 | Bentle et al. | 530/399 |
| 4,766,224 | 8/1988 | Rausch | 530/412 |
| 4,831,120 | 5/1989 | Aviv et al. | 530/399 |

FOREIGN PATENT DOCUMENTS

0173215 A2 3/1986 European Pat. Off. .
0208539 A2 1/1987 European Pat. Off. .

OTHER PUBLICATIONS

Hermann et al., 1983, J. of Biol. Chem. 258(18):11014-11019.
Marston, F. A. O., 1986, Biochem. J. 240(1):1-12.

Primary Examiner—Margaret Moskowitz
Assistant Examiner—Keith C. Furman
Attorney, Agent, or Firm—Brian K. Stierwalt; Larry R. Swaney; James W. Williams, Jr.

[57] ABSTRACT

A method of recovering biologically active somatotropins which are produced as insoluble refractile bodies in transformed microorganisms which comprises dissolving refractile bodies in a denaturant and 2-amino-2-methyl-1-propanol, homogenizing, and diluting to fold.

17 Claims, No Drawings

METHOD OF FOLDING SOMATOTROPINS

BACKGROUND OF THE INVENTION

The invention relates to a method of folding recombinant somatotropins. Somatotropins are hormones which are secreted by the adenohypophysis (anterior lobe of the pituitary gland) and are known to affect the rate of skeletal growth and gain in body weight. Administration of somatotropin has been shown to cause an increase in milk production in lactating animals such as dairy cows and goats. With the advent of recombinant DNA technology, the ability to produce greater quantities of proteins, like somatotropins, in transformed microorganisms has been achieved. Nevertheless, greater amounts of protein production in some bacteria leads to bioinactive cytoplasmic aggregates containing partially folded and unfolded proteins, or both, typically referred to as inclusion bodies, or refractile bodies. For the many proteins that contain disulfide crosslinks, this problem is especially severe since bacteria used as recombinant hosts like the commonly used *Escherichia coli*, are not adapted to the process of sulfhydryl oxidation to the disulfide form.

The proper conformation of a protein is essential for biological activity. Therefore, protocols are developed to enable the partially folded and unfolded proteins, typically found in refractile bodies to properly fold into their biologically active conformation. Known procedures for folding proteins include the use of detergents like sodium dodecyl sulfate (SDS) as denaturing agents, see Rausch et al., U.S. Pat. No. 4,677,196. Seely, James E., U.S. Pat. No. 4,656,255, describes a process for recovering proteins that includes resolubilization of sidestream precipitates isolated from chromatography effluent. The use of an aqueous urea solution to solubilize refractile bodies containing somatotropin protein and naturation of the proteins in the urea solution was described in Bentle et al., U.S. Pat. No. 4,652,630. However, many of the known procedures result in slow folding rates, low yield and uneconomical operations. As demonstrated by this invention, it has been discovered that the use of 2-amino-2-methyl-1-propanol (AMP) can enhance the folding rate without sacrificing yields.

SUMMARY OF THE INVENTION

The invention is a method for folding somatotropin to recover biologically active somatotropin which is produced as insoluble refractile bodies in transformed microorganisms. The use of the amine 2-amino-2-methyl-1-propanol (AMP) overcomes the inverse dependence that pH has on folding rate and protein yield. Different pH levels benefit either the rate of folding or yield of folded protein at the expense of the other. In the process of the invention AMP is employed to achieve both a rapid folding rate of somatotropin and recovery of biologically active somatotropin in high yield.

The following terms are defined as used herein. "Biologically active" refers to effecting an intended in vivo physiological response. "Somatotropin" is used to include, but is not limited to, mammalian somatotropins such as human, ovine, porcine, avian and bovine somatotropin. In addition to the invention being suitable for naturally occurring sequences of somatotropins, the invention is also applicable to analogs and homologs of the naturally occurring protein having somatotropin-like biological activity. To the extent other proteins are equivalents for purification purposes, the invention includes such proteins. "Denaturation" refers to a reversible change in conformation and a loss of secondary and tertiary structure that may be associated with changes in solubility, physical properties and biological activity. "Folding" refers to the process in which a protein obtains its proper three-dimensional conformation and native biologically active form. "Refractile bodies" is used to refer to cytoplasmic aggregates containing the somatotropin to be recovered. Furthermore, "host" refers to microbial cells such as animal and plant cells and bacteria and yeast cells which are capable of expressing or have been transformed to express somatotropin.

Prior to this invention, increasing the rate of protein folding without sacrificing yields, has been difficult to obtain. This difficulty is attributed to the phenomenon that folding rates and folding yield often have an inverse dependence on pH. In other words, at a pH of 9–10 the folding rate may increase, but a significant fraction of protein may aggregate and not fold. Conversely, at a higher pH of 11.0, the folding rate may be slower, but the amount of the protein that aggregates may be significantly less, therefore, higher folding yields can be obtained. These difficulties are overcome by the process of the invention and the use of AMP.

Mammalian somatotropins are preferred embodiments of this invention. Bovine somatotropin and porcine somatotropin are more preferred embodiments of this invention. It is contemplated that reference to such proteins is not limited to the entire amino acid sequence of the natural protein. Such references are intended to include fragments of the proteins, various deletions involving the proteins and various substitutions and modifications thereof. As long as the alteration of the proteins does not destroy the biological activity, it is contemplated that such altered proteins are included in the references to bovine and porcine somatotropins, such as methionyl bovine somatotropin and methionyl porcine somatotropin.

Typically, somatotropins contain approximately 191 amino acid residues and have an approximate molecular weight of 22,000 daltons. The complete amino acid sequences for somatotropins from several species are known, including the sequences for humans and animals such as birds (avian), sheep (ovine), pig (porcine) and cattle (bovine). A comparison of the amino acid sequence from the species listed above indicates a relatively high overall homology when considering "conservative" amino acid replacements. In general terms, some "conservative" substitutions can occur without substantial change in the gross chemical properties of a protein. Exemplary of such substitutions are substitution of aliphatic hydrophobic residues for one another (isolecine, valine, leucine and methionine) and substitution of polar residues for one another (arginine for lysine, glutamine for asparagine and glutamic acid for aspartic acid). Moreover, substitutions that are "radical" (representing different kinds of side chains) can occur without substantial change in function or chemical properties when the locus of substitution is not critical for conformation and the degree of substitution is not extensive.

It has been reported that most heterologous proteins expressed in *Escherichia coli* bacteria are aggregated, in varied extent following expression, as refractile bodies within the cytoplasm of the bacteria. While not fully understood, this is believed to result, at least in part, from the overproduction of the heterologous protein and insolubility in the host cell. Heterologous somatotropins are believed to be present in the refractile bodies in substantially reduced form (without disulfide linkages) due to the relatively high redox potential of the *E. coli* cell. The process of the invention is particularly advantageous to proteins produced by such recombinant means in bacteria because it allows for the proper folding and resulting bioactivity of the proteins expressed as bioinactive refractile bodies.

Numerous somatotropins have been expressed in *Escherichia coli* bacteria. For example, human somatotropin (*E. coli* K12 strain W3110/p107) is disclosed in U.S. Pat. No. 4,342,832; bovine somatotropin (*E. coli* K12 strain W3110/pBgh-1) is disclosed in European Patent Application Publication No. 75,444A (U.S. application Ser. No. 303,689, filed 9/18/81); porcine somatotropin as disclosed in European Patent application Publication No. 111,389A (U.S. application Ser. No. 439,977, filed 11/8/1981); and avian somatotropin is disclosed in PCT Application Publication Number W084/01150 filed Sept. 13, 1983. The particular host used for purposes of producing a recombinant somatotropin in refractile bodies is not critical to the invention.

Procedures for recovering refractile bodies from cells like *Escherichia coli* are known. Procedures include mechanical disruption, physical disruption, chemical disruption and enzymatic disruption. Specific means include the use of freezing/thawing, abrasion, sonication, detergents, osmotic shock, alkali treatment, heat, lysozyme, proteinase K and pepsin. The particular procedure for obtaining the protein aggregates is not critical to the invention.

The refractile body is generally separated from the remaining cellular debris, like cell wall fragments, by means of centrifugation or filtration. After the protein aggregate is obtained substantially free of cellular debris, the protein aggregate is suspended in water and centrifuged.

Typically, refractile bodies are solubilized under alkaline conditions in the presence of a denaturant, such as urea, and folded under milder conditions of lower pH and lower denaturant concentration with air oxidation. However, as previously mentioned, folding rate and folding yield have inverse dependence on pH. When the pH is between 9-10, rapid folding is obtained, however, yields are low. On the other hand, when pH is higher, yields are higher, however, the folding rate is slower. It has been discovered that the presence of AMP overcomes these difficulties, allowing rapid folding in high yields.

With the present invention, the pellet resulting from centrifugation is optionally washed with 2-amino-2-methyl-1-propanol (AMP). Washing with AMP enhances rapid folding rates. The concentration of AMP in the wash solution can range from about 0.05M to 0.3M with about 0.1M preferred. After washing, the refractile bodies are then solubilized with a denaturant in the presence of AMP. For best results, the concentration of AMP present with the denaturant ranges from about 0.01M to 0.2M with about 0.05M preferred.

Any denaturing reagent capable of completely but reversibly denaturing the proteins in the refractile bodies can be used. For example, about 3.0M to 6.0M guanidine-HCL, about 4.0M to 8.0M urea and about 0.03M to 0.5M sodium dodecyl sulfate are denaturing reagents commonly employed. The pH of the denaturing solution is adjusted in the range of about 9.5 to 11.5 with a range of about 10 to 11.5 preferred and pH of about 11.5 more preferred. High pH favors higher folding yield. The pH may be adjusted by using a variety of reagents including sodium hydroxide (NaOH), potassium hydroxide (KOH), AMP and other amines.

The washed refractile body solution is then homogenized. Homogenization can occur over a period of 30 seconds to 5 minutes. A preferred homogenization period is one minute. Homogenization plays an important role in potentiating the effect of AMP on the folding rate. While not wishing to be bound or limited by theory, it is believed that homogenization further removes impurities from the refractile bodies that may have an effect on the folding rate. The homogenized solution is optionally incubated (maintained) for a few minutes at room temperature. The short incubation period enhances the folding rate. Folding takes place over a period of 2 to 3 hours by diluting the homogenized solution with water or suitable buffer of the proper pH, like tris(hydroxymethyl)amino methane (Tris) or AMP. Suitable pH is in the range of about 9.5 to 11.5 with a range of about 10 to 11.5 preferred and pH of about 11.5 more preferred. The method results in an improved folding efficiency (ratio of the area of the oxidized peak to the total area of somatotropin using the HPLC assay) over a period of 2 to 3 hours. All of the above-mentioned steps are carried out at room temperature, although higher or lower temperatures may be used. A temperature of 5° C. to 30° C. is generally suitable, with room temperature preferred.

A reducing reagent is generally used to prevent the formation of intermolecular disulfide bonds in aggregated proteins. Optionally, a variety of reducing reagents may be used, for example, glutathione, $\beta$-mercaptoethanol, dithiothreitol (DTT) and dithioerythritol (DTE). In the case of bovine somatotropin, DTT showed no effect in reducing the amount of aggregate protein formed. This is only an indication that the particular protein aggregates were not likely to be due to intermolecular disulfide bonding and, therefore, the use of reducing reagents are not necessary when folding bovine somatotropin.

The concentration of somatotropin to be folded can be varied. Suitable concentrations of somatotropin range from 0.1 to 10.0 mg/mL, preferably 0.2 to 2.0 mg/mL, more preferably 0.3 to 1.0 mg/mL. The determination of aggregated somatotropin is determined by fractionating on a reverse phase high performance liquid chromatograph (HPLC) and integrating the area of the corresponding peaks assuming an extinction coefficient of $2.38 \times 10^5 M^{-1}.cm^{-1}$ at 215 nm or 15,000 $M^{-1}.cm^{-1}$ at 227 nm. Other known methods may be used to calculate the concentration. The concentration of somatotropin has a clear effect on improving folding yield. When the amount of somatotropin is increased, the amount of aggregate increases. Thus, aggregate formation is dependent on somatotropin concentration, however, the folding rate is not.

Folding activity is monitored by periodic sampling of the protein solution and assaying on a high performance liquid chromatograph. Folding can also be determined by other assays like radioimmunoassay, radio receptor binding assays and size exclusion chromatography.

PREFERRED EMBODIMENTS

The following examples illustrate specific embodiments of the invention described herein.

EXAMPLE 1

The invention is demonstrated by solubilization of N-methionyl bovine somatotropin (MBS) expressed in *E. coli* as described in U.S. Pat. No. 4,652,630. Harvested cells are disrupted by double passage through a "Manton Gaulin" homogenizer. Refractile bodies, containing MBS, are pelleted from the homogenate solution by low speed centrifugation at 12,000×g for about 5 minutes.

About 0.5 grams of refractile bodies containing 100 mg of reduced methionyl bovine somatotropin are suspended in 20 mL water. Two mL of the suspension are centrifuged at 14000×g for 10 minutes at about 4° C. in a "RC5B SORVAL" refrigerated centrifuge.

The refractile body pellet obtained from centrifugation is washed in 25 mL of about 0.1M AMP (Sigma, St. Louis, Mo.). The washed suspension is centrifuged again at 14000×g for 10 minutes at about 4° C.

The pellet obtained from centrifugation is dissolved in 100mL of 0.05M AMP containing 7.5M urea and 0.0001M dithiothreitol (DTT) (Sigma, St. Louis, Mo.) and homogenized for one minute at about 24°-28° C. using a "POLYTRON" PT-20/35 (Brinkman Instruments, Westbury, N.Y.) on a setting of 2. The pH of the solution is adjusted to pH 11.5 with 1N NaOH. The solution is incubated for 10 minutes at 22°-23° C.

The somatotropin is folded by diluting the solution with water at about 22°-23° C. to final concentrations of 4.5M urea and 0.03M AMP. Folding is completed over a period of 2-3 hours.

The folding rate of reduced bovine somatotropin is monitored by periodic sampling of 0.1 mL of the folding solution. The sample is injected directly into a high performance liquid chromatograph (HPLC). The HPLC assay uses a 4.1×250 mm "SYNCHROPAK" RP-8 column (Synchrom, Inc., Lafayette, Ind.) equilibrated with 52% acetonitrile containing 0.3% trifluoroacetic acid (TFA) with a typical gradient as follows:

| TIME | FLOW (mL/min) | % A | % B |
| --- | --- | --- | --- |
| 0.0 | 2.000 | 48 | 52 |
| 6.0 | 2.000 | 35 | 65 |
| 6.1 | 2.000 | 20 | 80 |
| 9.6 | 2.000 | 20 | 80 |
| 9.7 | 2.000 | 48 | 52 |

A = H₂O/0.3% TFA
B = Acetonitrile/0.3% TFA

EXAMPLE 2

The effect of 2-amino-2-methyl-1-propanol on the folding rate of MBS is compared to Tris (hydroxymethyl)-amino methane and compared to control (without amine) at the same pH levels. The experiment is carried out in substantial accordance with the teaching of Example 1. The results are shown in Table 1.

TABLE 1

|  | pH | Folding Rate (Amt. folded after 1 hour) |
| --- | --- | --- |
| 30mM 2-amino-2-methyl-1-propanol (AMP) | 11.0 | 87% |
| 30mM Tris (hydroxymethyl)-amino methane | 11.0 | 40% |
| Control (1mM NaOH) | 11.0 | 37% |

The use of AMP results in faster folding rates.

EXAMPLE 3

The effect of using 2-amino-2-methyl-1-propanol and pH is evaluated by following the procedure of Example 1 and varying the reagent in the dissolving step by using 50 mM Tris and NaOH. The results are shown in Table 2.

TABLE 2

|  | pH | Folding Yield | Folding Rate (Amt. folded after 1 Hour) |
| --- | --- | --- | --- |
| 30mM 2-amino-2-methyl-1-propanol (AMP) | 11.0 | 86% | 87% |
| 30mM Tris (hydroxymethyl)-amino methane | 9.4 | 64% | 54% |
| Control (1mM NaOH) | 11.0 | 87% | 37% |
| 30mM Tris (hydroxymethyl)-amino methane | 11.0 | 85% | 40% |

High pH favors a high folding yield but not a rapid folding rate, except when AMP is used, resulting in both high folding yield and high folding rate.

EXAMPLE 4

The effect of the concentration of somatotropin on folding yield is evaluated by following the procedure of Example 1 and varying the amount of somatotropin to be folded. The results are shown in Table 1.

TABLE 3

| MBS (mg/mL) | Correctly Folded MBS |
| --- | --- |
| 0.6 | 90% |
| 0.8 | 87% |
| 3.3 | 80% |
| 8.7 | 70% |

The data shows that the amount of correctly folded somatotropin is dependent on the concentration of somatotropin.

Although the invention has been described with respect to specific modifications, the details thereof are not to be construed as limitations, for it will be apparent that various equivalents, changes and modifications may be resorted to without departing from the spirit and scope thereof and it is understood that such equivalent embodiments are to be included therein.

What is claimed is:

1. A method for folding and recovering biologically active somatotropin which is produced as insoluble refractile bodies in a transformed microorganism, which method comprises:
   (a) dissolving refractile bodies in a solution comprising a denaturant and 2-amino-2-methyl-1-propanol;
   (b) homogenizing the solution of step (a); and
   (c) diluting the solution of step (b) to fold the somatotropin into its biologically active conformation.

2. The method of claim 1 in which the somatotropin is selected from the group consisting of ovine somatotropin, bovine somatotropin, human somatotropin, porcine somatotropin and avian somatotropin.

3. The method of claim 1 in which the somatotropin is bovine somatotropin.

4. The method of claim 1 in which the somatotropin is porcine somatotropin.

5. The method of claim 1 in which the refractile bodies are first washed in a solution comprising 2-amino-2-methyl-1-propanol.

6. The method of claim 5 in which the concentration of 2-amino-2-methyl-1-propanol in the wash solution is from about 0.05M to 0.3M.

7. The method of claim 1 in which the concentration of 2-amino-2-methyl-1-propanol in step (a) is from about 0.01M to 0.2M.

8. The method of claim 1 in which the pH of the solution in step (a) is from about 9.5 to 11.5.

9. The method of claim 1 in which the concentration of somatotropin in step (c) after dilution, is about 0.1 mg/mL to 10 mg/mL.

10. The method of claim 1 in which the solution in step (c) is diluted with a reagent selected from the group consisting of water, tris(hydroxymethyl) amino methane and 2-amino-2-methyl-1-propanol.

11. The method of claim 10 in which the reagent is water.

12. The method of claim 10 in which the denaturant is urea and the solution in step (c) is diluted to a final concentration of about 2.4M to 5.0M urea.

13. The method of claim 1 in which the denaturing reagent is selected from the group consisting of guanidine-HCl, urea and sodium dodecyl sulfate.

14. The method of claim 13 in which the denaturing reagent is about 4.0M to 8.0M urea.

15. A method for recovering biologically active somatotropin which is produced as insoluble refractile bodies in a transformed microorganism, which method comprises:
(a) washing refractile bodies with about 0.05M to 0.3M 2-amino-2-methyl-1-propanol;
(b) dissolving the washed refractile bodies in a solution comprising a denaturant of about 4.0M to 8.0M urea and about 0.01M to 0.2M 2-amino-2-methyl-1-propanol;
(c) adjusting the solution of step (b) to a pH of about 9.5 to 11.5;
(d) homogenizing the solution of step (c);
(e) incubating the homogenized solution of step (d); and
(f) diluting the solution of step (e) to a final concentration of about 2.4M to 5.0M urea to fold the somatotropin into its biologically active conformation to obtain about 0.1 mg/mL to 10.0 mg/mL active somatotropin.

16. The method of claim 15 in which the somatotropin is bovine somatotropin.

17. The method of claim 15 in which the somatotropin is porcine somatotropin.

* * * * *